US006881573B2

(12) United States Patent
Louderback

(10) Patent No.: US 6,881,573 B2
(45) Date of Patent: Apr. 19, 2005

(54) AUGMENTED SOLVENT/DETERGENT METHOD FOR INACTIVATING ENVELOPED AND NON-ENVELOPED VIRUSES

(76) Inventor: Allan L. Louderback, 9661 Longden Ave., Temple City, CA (US) 91780

( * ) Notice: Subject to any disclaimer, the term of this patent is extended or adjusted under 35 U.S.C. 154(b) by 31 days.

(21) Appl. No.: 10/661,329

(22) Filed: Sep. 12, 2003

(65) Prior Publication Data

US 2005/0059143 A1 Mar. 17, 2005

(51) Int. Cl.[7] .................. A61K 39/395; C07H 21/04
(52) U.S. Cl. .................. 435/320.1; 435/69.1; 435/6; 530/350; 424/147.1
(58) Field of Search .................. 435/320.1, 69.1, 435/6, 252.3, 7.1, 325; 530/350; 424/147.1, 141.1; 536/23.5

(56) References Cited

U.S. PATENT DOCUMENTS

| | | | |
|---|---|---|---|
| 4,305,871 A | 12/1981 | Shanbrom | |
| 4,314,997 A | 2/1982 | Shanbrom | |
| 4,315,919 A | 2/1982 | Shanbrom | |
| 4,412,985 A | 11/1983 | Shanbrom | |
| 4,481,189 A | 11/1984 | Prince | |
| 4,591,505 A | 5/1986 | Prince | |
| 4,764,369 A * | 8/1988 | Neurath et al. .......... | 424/176.1 |
| 4,833,165 A | 5/1989 | Louderback | |
| 4,909,940 A | 3/1990 | Horowitz | |
| 5,094,960 A | 3/1992 | Bonomo | |
| 5,120,649 A | 6/1992 | Horowitz et al. | |
| 5,186,945 A | 2/1993 | Shanbrom | |
| 5,648,472 A | 7/1997 | Gehringer et al. | |
| 5,981,163 A * | 11/1999 | Horowitz et al. .......... | 435/4 |
| 6,214,534 B1 * | 4/2001 | Horowitz et al. .......... | 435/2 |
| 6,372,216 B1 | 4/2002 | Piazza | |
| 6,468,733 B1 * | 10/2002 | Nur et al. .......... | 435/2 |
| 6,514,987 B1 | 2/2003 | Cook et al. | |
| 6,548,242 B1 * | 4/2003 | Horowitz et al. .......... | 435/2 |

OTHER PUBLICATIONS

Ager, A.; Anderson, SL; Louderback AL; Milhous, WK; Formaldehyde/Detergent Solution Prevents Blood Borne Transmission of [Plasmaodium] Infection in a Mouse Model, *American Society of Tropical Medicine and Hygiene*, Abstract Submission Form, Annual Meeting, 1991.

Ehud Ben–Hur, Bernard Horowitz, Virus Inactivation in Blood, Editorial Review, *AIDS 1996, 10:1183–1190*, Rapid Science Publishers ISSN 0269–9370.

Chen, SX; Hammond, DJ; Lang, JM; Lebing, WR; Purification of $\alpha_1$ Protinase Inhibitor from Human Plasma Fraction IV–1 by Ion Exchange Chromatography; *Vox Sanguinis*, 1998: 74(4): 232–241.

Chen, SX; Hammond, DJ; Klos, AM; Wood, DW; Wydick, JE; Lebing, WR; Chromatography Purification of human $\alpha_1$ Proteinase Inhibitor from Dissolved Cohn Fraction IV–1 Paste; Journal of Chromatography A. 800 (2) (1998): 207–218.

Highsmith, F; Xue, H; Chen, X; Benade, L; Owens, J; Shanbrom, E; Drohan, W; Iodine–mediated Inactivation of Lipid– and Nonlipid–enveloped Viruses in Human Antithrombin III Concentrate; *Blood*, vol. 86, No. 2, (Jul. 18, 1995); pp. 791–798.

(Continued)

*Primary Examiner*—Gregory Webb
(74) *Attorney, Agent, or Firm*—Gale Thorne

(57) ABSTRACT

A process for making Solvent Detergent (SD) treatment effective against non-enveloped viruses. The process stipulates using prequalified concentrations of formaldehyde and phenol with SD treatments. In particular, serial or combined use of 100 to 10,000 parts per million of formaldehyde and/or 100 to 10,000 parts per million of phenol with an associated SD treatment process are disclosed.

36 Claims, 2 Drawing Sheets

OTHER PUBLICATIONS

Highsmith, FA; Xue, H; Caple, M; Walthall, B; Drohan, WN, Shanbrom, E; Inactivation of Lipid–Enveloped and Non–lipid–enveloped Model Viruses in Normal Human Plasma by Crosslinked Starch–iodine: *Plasma Derivatives Department, Holland Laboratory, American Red Cross, Rockville, Maryland, and Irvine Scientific Incorporated, Santa Ana, California;* received for publication Aug. 26, 1993, revised No. 16, 1993 and accepted Nov. 22, 1993; published in *Transfusion*, 1994; vol. 34, No. 4, pp. 322–327.

Highsmith, FA; Caple, M; Walthall, B; Shanbrom, E; Drohan, WN; Viral Inactivation of Vasicular Stomatitis Virus in Normal Human Serum by Cross–Linked Polyvinylpyrrolidone; *The Journal of Infectious Diseases,* 1993;167:1027–33, published by The University of Chicago.

Horowitz, B; Prince, AM; Hamman, J; Watklevicz,C; Viral Safety of Solvent/Detergent–treated Blood Products; *Blood Coagul. Fibrinolysis*. 1994 Dec; 5 Suppl 3: S21–28. See Abstract for safety of S/D products; p. S22 for viral safety in formal clinical trials and Tables 1 and 2.

Horowitz, B; Pathogen Inactivated Transfusion Plasma: Existing and Emerging Methods, a proceedings paper from *Vox Sanguinis (Vox Sang 2002: 83, (Suppl. 1): 429–436.*

Horowitz, B; Ben–Hur, E; Efforts in Minimizing Risk of Viral Transmission through Viral Inactivation; *The Finish Medical Society Duodecim, Ann. Med. 2000, 32: 475–484.*

Horowitz, B; Lazo, A; Grossberg, H; Page, G; Lippin, A; Swan, G.; Virus Inactivation by Solvent/Detergent Treatment and the Manufacture of SD–Plasma; *Vox Sanguinis, Lunch Symposium Paper;* Vox Sang. 1998, 74 Suppl. 1;: 203–206.

Horowitz, B; Prince, AM; Hamman, J; Watklevicz, C; Viral Safety of Solvent/Detergent–treated blood products—Abstract; *Dev Biol Stand. 1993;81: 147–161.*

Korneyeya, M; Hottta, J; Lebing, W; Rosenthal, RS; Franks, L; Petteway, SR Jr.; Enveloped Virus Inactivation by Caprylate: a Robust Alternative to Solvent–Detergent Treatment in Plasma Derived Intermediates; *Biologicals, Jun. 2002; 30(2): 153–62.*

Lebing, WR; Hammond, DJ; Wydick, JE III, Baumbach, GA; A Highly Purified Antithrombin III Concentrate Prepared from Human Plasma Fraction IV–1 by Affinity Chromatography; Vox Sanguinis, *Vox Sang.*, 1994; 67(2): 117–124.

Lebing, W; Remington, KM; Schreiner, C; Paul, I; Properties of a New Intravenous Immunoglobulin (IGIV–C, 10%) Produced by Virus Inactivation with Caprylate and Column Chromatography; copyright Blackwell Publishing, Ltd., Vox Sanguinis (2003): 84(3), 193–201.

Lee, DC; Stenland, CJ; Miller JLC; Cai, K; Ford, EK; Gilligan, KJ; Hartwell, RC; Terry, JC; Rubenstein, R; Fournel, M; Petteway SR Jr.; A Direct Relationship between the Partioning of the Pathogenic Prion Protein and Transmissible Spongiform Encephalopathy Infectivity during the Purification of Plasma Proteins; *Transfusion,* 2001: 41(4): 449–455.

Louderback, A; A Protocol for Sterilization of Blood for Transfusion; Oral presentation at the $5^{th}$ National Forum on AIDS, Hepatitis and other Blood Borne Diseases; CDC Meeting, Atlanta, GA on Mar. 30, 1992.

Louderback, A; Sterilization of Red Blood Cells for Transfusion; *Speech at $45^{th}$ AABB Meeting in San Francisco, Nov. 11, 1992*.

Miller. JLC; Petteway, SR Jr; Lee, DC; Ensuring the Pathogen Safety of Intravenous Immunoglobulin and Other Human Plasma–derived Therapeutic Proteins; *Journal of Allergy Clinical Immunology, Oct. 2001 V. 108, pp. S91–4 (Figure S92).*

Robinson, S; Schwinn, H; Josic, D; Nur, I; Stradler, M; Bal, F; Gehringer, W; Schutz, R; Development and Biochemical Characterization of a Double–virus–inactivated Factor VIII Preparation, *Blood Coagulation and Fibrinolysis, Vol. 6, Suppl. 2, 1995,* copyrighted by Rapid Science Publishers; pp. S40–47.

Schwinn, H; Stadler, M; Josic, DJ; Bal, F; Gehringer, W; Nur, I: Schütz, R; A Solvent 1 Detergent Treated, Pasteurised and Highly Purified Factor VIII Concentrate; *Arzneim.–Forsch./Drug Res. 44(1) , Nr. 2 (1994) pp. 188–191 (English and German).*

Stenland, CJ; Lee, DC; Brown, P; Petteway SR Jr.; Rubenstein, R; Partitioning of Human and Sheep Forms of the Pathogenic Prion during the Purification of Therapeutic Proteins from Human Plasma, *Transfusion, vol. 42(11), Nov. 2002, pp. 1497–1500.*

Trejo, SR; Hotta, JA; Lebing, W; Stenland, C; Storms, RE; Lee, DC; Petteway, LS Jr.; Remington, KM; Evaluation of Virus and Prion Reduction in a New Intravenous Immunoglobulin Manufacturing Process; *Vox Sanguinis (2003) 84, 176–187,* copyrighted by Blackwell Publishing, Ltd.

Prince, AM; Blood Products; *Nature. Jan. 4, 1996; 379 (6560)*:14. See entire article.

Cai, K; Miller, JL; Stenland, CJ; Gilligan, KJ; Hartwell, RC; Terry, JC; Evans–Storms, RB; Rubenstein, R; Peteway, SR Jr.; Lee, DC; Solvent–dependent Precipitation of Prion Protein. *Biochimica et Biophysica Acta. May 20, 2002; 1597(1): 28–35,* See Abstract plus p. 32 (Figure 4) and p. 33 (Figures 5 and 6).

* cited by examiner

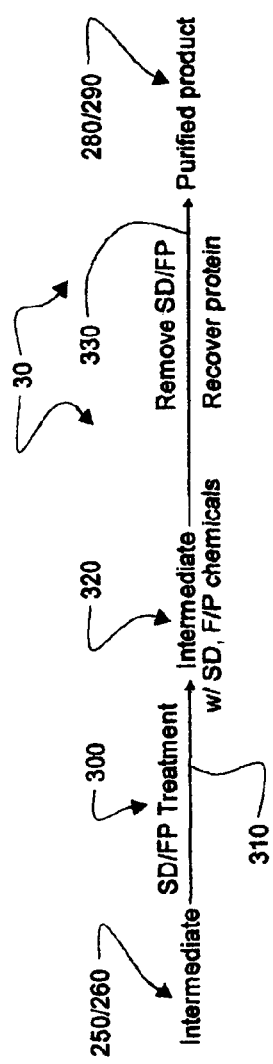
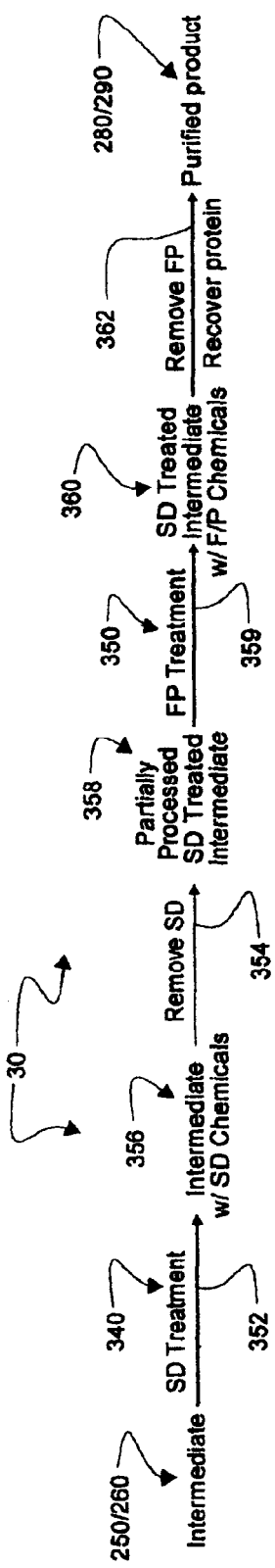
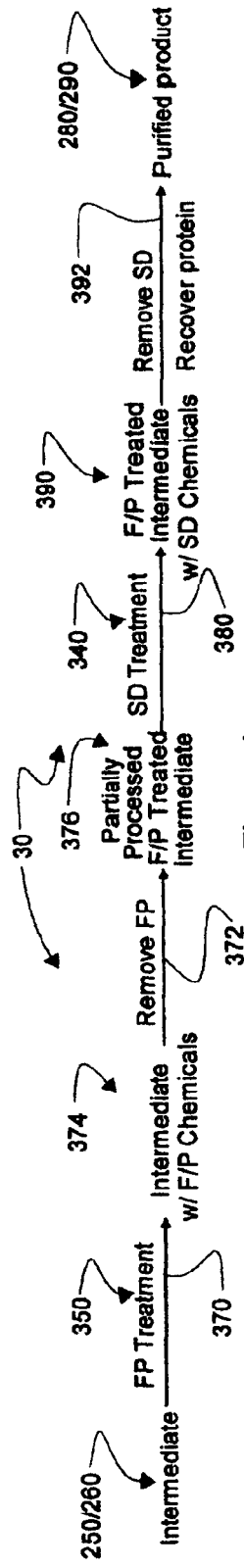
Figure 2
Figure 3
Figure 4

AUGMENTED SOLVENT/DETERGENT METHOD FOR INACTIVATING ENVELOPED AND NON-ENVELOPED VIRUSES

FIELD OF INVENTION

This invention relates to methods for sterilizing and/or depyrogenating products and materials used in the biomedical field and, in particular, to inactivating enveloped and non-enveloped viruses in plasma derived pharmaceuticals.

BACKGROUND OF THE INVENTION

Solvent/Detergent (SD) treatment of plasma and plasma derivatives to inactivate viruses is well known in the art of eliminating pathogens and depyrogenating plasma derived pharmaceuticals. SD treatment of plasma to inactivated lipid enveloped viruses is also well known. Various SD treatments are described, for example, in U.S. Pat. Nos. 4,315,919 titled DEPYROGENATION PROCESS, issued Feb. 16, 1982 to Shanbrom (Shanbrom '919); 4,412,985, titled DEPYROGENATION PROCESS, issued Nov. 1, 1983 to Shanbrom (Shanbrom '4,481,189, titled PROCESS FOR PREPARING STERILIZED PLASMA AND PLASMA DERIVATIVES, issued Nov. 6, 1984 to Prince (Prince '189); 4,591,505, titled PROCESS FOR INACTIVATING HEPATITIS B VIRUS, issued May 27, 1986 to Prince (Prince '505); 4,764,369, titled UNDENATURED VIRUS-FREE BIOLOGICALLY ACTIVE PROTEIN DERIVATIVES, issued Aug. 16, 1988 to Neurath, et al. (Neurath '369); 4,909,940, titled EXTRACTION OF PROCESS CHEMICALS FROM LABILE BIOLOGICAL MIXTURES WITH ORGANIC ALCOHOLS OR WITH HALOGENATED HYDROCARBONS, issued Mar. 20, 1990 to Horowitz, et al. (Horowitz '940); 5,094,960, titled REMOVAL OF PROCESS CHEMICAL FROM LABILE BIOLOGICAL MIXTURES BY HYDROPHOBIC INTERACTION CHROMATOGRAPHY, issued Mar. 10, 1992 to Bonomo (Bonomo '960); and 5,186,945 titled BLOOD PLASMA ANTIVIRAL PROCESS AND COMPOSITION, issued Feb. 16, 1993 to Shanbrom (Shanbrom '945).

Separation of SD chemicals from the plasma intermediates after SD treatment is described in U.S. Pat. Nos. 5,120,649, titled PHOTODYNAMIC INACTIVATION OF VIRUSES IN BLOOD CELL-CONTAINING COMPOSITIONS, issued Jun. 9, 1992, to Horowitz, et al. (Horowitz 649), Shanbrom '945; 5,648,472, titled PROCESS FOR PREPARING VIRUS-INACTIVATED IMMUNOGLOBULIN SOLUTIONS, issued Jul. 15, 1997, to Gehringer, et al. (Gehringer '472); 6,372,216 titled METHOD OF PRODUCING SPECIFIC IMMUNOGLOBULIN TO BLOCK HCV INFECTION, issued Apr. 16, 2002 to Piazza (Piazza '216); 6,468,733 titled METHOD OF THE INACTIVATION OF VIRUSES BY A SOLVENT-DETERGENT COMBINATION AND NANOFILTRATION issued Oct. 22, 2002 to Nur. et al. (Nur '733); and 6,517,987 titled FRANGIBLE COMPOUNDS FOR PATHOGEN INACTIVATION issued Feb. 4, 2003 to Cook et al. (Cook '987). Each manufacturer of such plasma products may use slightly different detergents and conditions in the SD treatment. It should be noted that different removal techniques may be used by the different manufacturers depending upon the specific process utilized and/or products involved.

In order to assure the safety of blood products against non-enveloped viruses, a second viral inactivation (e.g. pasteurizaiton, dry-heat) or a removal step is currently, usually employed (e.g. fractionation). There is, to date, no inactivation method effective against prions, including any of the currently used methods which preserve the activity of therapeutically active proteins. Fractionation is the only known effective removal step as reported in Vox Sanguinis, Blackwell Publishing, Ltd, 84, 174–187, 2003.

It has been shown that formaldehyde and/or phenol inactivates both enveloped and non-enveloped viruses. Use of formaldehyde/phenol in an SD treated product would assure enveloped and non-enveloped virus inactivation. However, currently such treatments must be done independently resulting in longer process time and handling losses. As Prince '189 teaches, "For instance, it is known to attempt to inactivate hepatitis B virus by contact with an aldehyde such as formaldehyde whereby crosslinking to the protein is effected and the hepatitis B virus is inactivated."

Louderback '165 teaches inactivating HTLV-III virus in blood or blood components by treatment with phenol, formaldehyde or mixtures thereof. However, use of formaldehyde has, in the past, not been considered suitable for inactivation of viruses in plasma, as is taught in Prince '189, "It is to be understood that the problems of inactivation of hepatitis in plasma are distinct from the problems of inactivation of the viruses themselves due to the copresence of the desirable components of the plasma. Thus, while it is known how to inactivate the hepatitis B virus, crosslinking agents, e.g. glutaraldehyde, nucleic acid reacting chemical e.g.: BPL [beta propiolactone], or formaldehyde, or oxidizing agents e.g. Clorox etc. it has been believed that these methods are not suitable for the inactivation of the virus in plasma due to the observation that most of these inactivating agents (sodium hypochlorite, formaldehyde, .beta.-propiolactone) denature the valuable proteinaceous components of the plasma."

For each SD treatment and associated SD chemical separation, it is normal practice to set up a standard protocol which is particularly specified for each SD treatment. To minimize training and related documentation, it is preferred that any augmentation of such treatments and separations require little or no effect on the specified standard protocol.

For an augmented SD treatment which inactivates both enveloped and non-enveloped viruses to be effective, the SD and augmenting portion of the treatment should, therefore, be able to be performed simultaneously, effecting rapid enveloped and non-enveloped viral kill and, potentially, prion inactivation. Removal of all reagents, so employed, at the end of a blood plasma process intermediates treatment should be accomplished by standard methods, e.g. precipitation or chromatography to recover the therapeutic proteins. It would be advantageous, as well, for incubation to be at the temperature and for the times necessary for the effectiveness of SD treatment, for example 27° C. (±3° C.) for 6 hours. Typical concentrations in the final plasma mixture of the SD chemicals would be Triton X-100—0.5% to 1.0% (5000–10,000 ppm), and/or Tween-80—0.5%–1.0% (5000–10,000 ppm) and Tri-n-Butyl Phosphate—0.3% (3000 ppm).

Louderback in U.S. Pat. No. 4,833,165, titled METHOD OF INACTIVATING HTLV-III VIRUS IN BLOOD issued May 23, 1989 to Louderback (Louderback '165) describes a sterilization treatment of washed red blood cells using a solution containing formaldehyde and/or phenol which was shown to be effective to inactivate HTLV-III (now called HIV-1) so that one could transfuse virally inactivated sterile treated red blood cells to a patient. Work with a variety of viruses and bacteria and parasitic protozoa showed likewise inactivation in so treated red blood cells permitting subsequent transfusion into a patient without risk of disease transmission.

A summary of viral inactivation data for the formaldehyde/phenol in red blood cells derived from Louderback '165, CDC (March 1992), and AABB (Nov. 1992)] is provided in Table I. Formaldehyde solution is very water soluble and hydrophilic. Phenol in solution is very lipid soluble and lipophilic. A combination of these two different sterilizing liquids acting upon both enveloped (having a lipid outer shelf) and non-enveloped viruses at the same time causes a synergistic action of inactivation gr ater than either alone. Treatm nt time used was 20–30 minutes at room temperature (20° C.±2° C.) with 3000 ppm formaldehyde and/or phenol.

TABLE I

|  | Log killed | genome | medium* |
|---|---|---|---|
| Enveloped Virus |  |  |  |
| HIV-1 | >=4.33 | RNA | rbc |
| FIV | all killed | RNA | rbc |
| Sindbis | >=6.71 | RNA | rbc |
| VSV | >=7.00 | RNA | rbc |
| CMV | >=5.23 | DNA | rbc |
| Vaccina | >=4.79 | DNA | rbc |
| Non-enveloped Virus |  |  |  |
| Polio virusType 1 | >=4.20 | RNA | plasma or rbc |
| Parvo virus B19 (human) | >=5.00 | DNA | plasma |
| Parvo virus (pig) | >=4.0 | DNA | plasma |

*rbc = red blood cells

Formaldehyde and/or phenol also inactivates bacteria and protozoans in blood cell mixtures. Table II, found hereunder, provides a summary of data for bacteria and parasitic protozoans.

TABLE II

Inactivation of Bacteria & Protozoans in Whole Blood

|  | Logs inactivated |
|---|---|
| Bacteria |  |
| Yersinia entercolitica | 2* |
| Treponema pallidum | 8* |
| Borrelia burgdorferi | 8* |
| Protozoans |  |
| Trypanosoma cruzi | 8–9* |
| Leishmania tropica | 6* |
| Plasmodium berghei | 8–9* |
| Babesia microti | 8* |

*all added organisms were inactivated

As used herein, the term "process intermediate" is defined to be a solution containing one or more therapeutic proteins, carbohydrates or glycoproteins that has been processed to produce a therapeutic product intended for administration to humans, animals or plants. A "process intermediate" may be derived from human or animal blood, plasma or plasma fractions; recombinant cells or culture media, tissue culture cells or media, cell culture cells or media, insect or other invertebrate cells or media or from any biological tissues or fluids.

BRIEF SUMMARY AND OBJECTS OF THE INVENTION

In brief summary, this invention provides novel and effective methods, which augment a variety of SD treatment procedures currently being made available through a diversity of SD treatment manufactures, for inactivating enveloped and non-enveloped viruses. These methods may be applied concurrently or serially without affecting standard protocol associated with a selected SD treatment method. Because the time and temperature for augmenting a selected SD treatment may be exactly the same as standard protocol specified by a SD treatment manufacturer, no major changes in that standard protocol are required. Also removal steps that are presently being specified by each manufacturer for the selected SD treatment remain essentially unchanged. As an example, for an SD treatment protocol employing a 27° C. or higher temperature for a time of six hours or longer, augmentation by adding a predetermined concentration of formaldehyde and/or phenol, according to the instant invention, provides a far broader spectrum of effective enveloped and non-enveloped virus inactivation than the SD treatment alone.

Note in Table II that treatment time was 20–30 minutes at room temperatures (20° C.±2° C.). As generalized standard protocol for SD treatment usually specifies a 27° C. incubation temperature over a period of six hours, which is higher and longer, respectively, than illustrated in Table II. Therefore, following a standard SD treatment protocol results in conditions which are even more effective for the formaldehyde and phenol treatment of the current invention for inactivation of viruses than was the case for studies related to Table II.

As earlier cited, typical concentrations in the final plasma mixture of the SD chemicals are Triton X-100—0.5% to 1.0% (5000–10,000 ppm), and/or Tween-80—0.5%–1.0% (5000–10,000 ppm) and Tri-N-Butyl Phosphate—0.3% (3000 ppm). Formaldehyde concentrations in a final plasma mixture, according to the instant invention, are formaldehyde at 0.3% (3000 ppm) and phenol at 0.3% (3000 ppm). These chemicals may be afterwards removed by precipitation (e.g. PEG 3350) or by column removal (e.g. binding IgG on CM Sephadex C-50). The proteins that are precipitated can be recovered and resuspended. Eluate fluid that goes through the column can be recovered and concentrated for final use.

It is presently preferred to add SD chemicals and the formaldehyde and/or phenol chemicals to a plasma process intermediate at the same time so that the sterilization action of both systems proceeds simultaneously for the shared same time period and temperature and later removal of the chemical sterilants.

However, in a first step of another method embodiment of the instant invention, an SD chemical mixture is added to the plasma process intermediate. A standard SD incubation period is implemented through a prespecified time-temperature period with SD sterilization chemicals being removed from the plasma process intermediate prior to adding a formaldehyde and/or phenol chemical mixture, according to the invention, to the already treated process intermediate as a second step. Included in the second step is a follow-on second incubation for the formaldehyde and/or phenol chemical mixture, as a secondary sterilizing step, and a following removal of second step sterilants.

In a third embodiment of the invention, formaldehyde and/or phenol chemicals are first added to the plasma process intermediate and the initial mixture is incubated through a time-temperature period followed by removal of the sterilization chemicals from the resulting process intermediate. Secondarily a SD chemical mixture is added to the already treated plasma process intermediate after which a standard time-temperature incubation period is employed followed by a sterilant removal step.

Note that, in the primary embodiment of the invention, SD and formaldehyde/phenol sterilant chemicals of both systems are added simultaneously. In other embodiments of the invention, chemicals of each system are added sequentially and processed sequentially. It does not matter which chemicals are added first or second, but it is necessary that both are used to treat the plasma process intermediate to assure inactivation of lipid enveloped and non-lipid enveloped viruses.

Accordingly, it is a primary object to provide a process for augmenting SD treatment of a process intermediate.

It is a principal object to provide a process for augmenting SD treatment of a process intermediate whereby non-enveloped viruses are inactivated.

it is a basic object to provide a process for augmenting a general set of SD treatments, for inactivating viruses within process intermediates, which is compatible with those SD treatments, but which inactivates a broader spectrum of viruses including non-enveloped viruses.

It is a further basic object to provide a process for augmenting such SD treatments without requiring changes to basic protocol used for the SD treatment.

It is an important object to provide a process for augmenting such SD treatments which may be used simultaneously with the SD treatment or non-concurrently, being applied serially rather than simultaneously.

It is a further object to provide processes, for augmenting such SD treatments, which are effective when incubation periods consistent with standard protocol for SD treatment are employed.

It is a further object to provide a process, for augmenting a commercially available SD treatment, which is effective with an incubation temperature consistent with a standard protocol of the SD treatment.

These and other objects and features of the present invention will be apparent from the detailed description taken with references to accompanying drawings.

BRIEF DESCRIPTION OF THE DRAWINGS

FIG. 2 is a flow chart outlining an exemplary process segment which may be implemented according to the instant invention for applying SD with a formaldehyde/phenol treatment at the points of application outlined in FIG. 1.

FIG. 3 is a flow chart which provides an exemplary alternative process for applying SD and a formaldehyde/phenol treatment at the points of application seen in FIG. 1.

FIG. 4 is a flow chart providing yet another exemplary process for applying SD and a formaldehyde/phenol treatment at the points of application illustrated in FIG. 1.

DETAILED DESCRIPTION OF THE INVENTION

Figure 1:
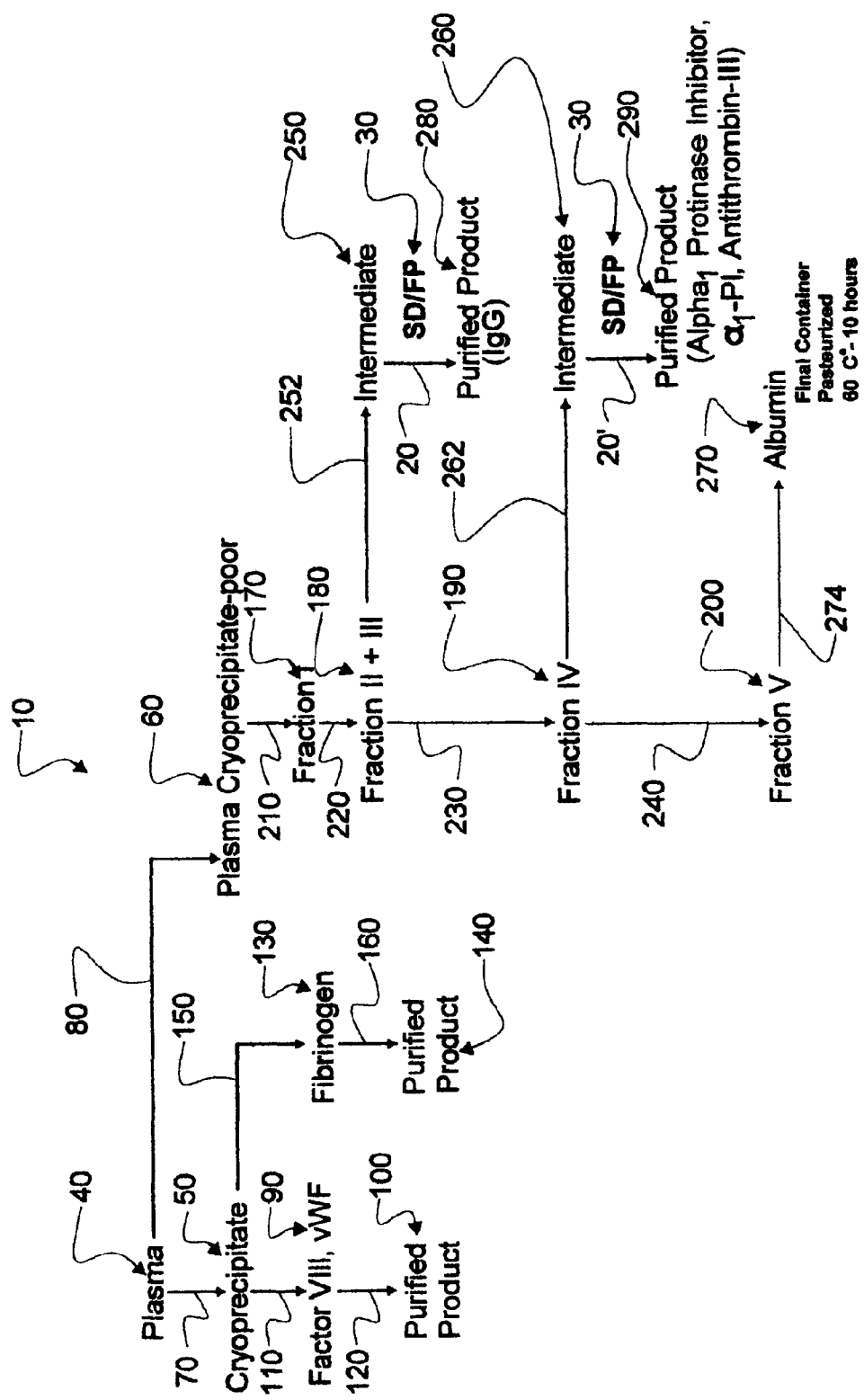
FIG. 1 is a flow chart outlining an example of the current Cohn-Oncley alcohol fractionation process, currently employed commercially for preparation of plasma d rivatives, including points of application where process intermediates ar treated with the solvent detergent (SD) and formaldehyde/phenol to inactivate enveloped and non-enveloped viruses according to the instant invention.

As disclosed supra, SD treatment of plasma derivatives to inactivates viruses and remove pyrogens is well known in the art of processing such products. SD treatment of process intermediates is widely used in blood treatment laboratories world-wide. With protocol and associated training already in place world-wide for SD treatment, it appears particularly prudent to provide a process which is compatible with a wide spectrum of SD treatments and which makes such treatments more effectively by inactivating non-enveloped viruses, something current SD treatments cannot do.

Reference is now made to FIG. 1, which is an outline of the current Cohn-Oncley alcohol fractionation process 10 modified to include points of application 20 and 20' of a combined SD and formaldehyde/phenol virus inactivation process, generally numbered 30, according to the instant invention. Process 10 is seen to include fractionation of plasma 40 into a cryoprecipitate 50 and cryoprecipitate-poor plasma fraction 60 as indicated by lines 70 and 80, respectively. As is standard in the Cohn-Oncley process, further fractionation of cryoprecipitate 50 yields factor VIII, von Willebrand Factor (vWF) 90 as depicted by line 110 and which is formulated into a purified product 100 as depicted by line 120. Fractionation of cryoprecipitate 50 also yields fibrinogen 130 and which is formulated into a purified product 140 via lines 150 and 160, respectively.

The Cryoprecipitate-poor plasma fraction 60 is further fractionated into a fraction 170 (Fraction I), a fraction 180 (Fractions II+III), a fraction 190 (Fraction IV) and a fraction 200 (Fraction V), as indicated in sequence by lines 210, 220, 230 and 240, respectively. Exemplary components of fraction 180 are IgG, IgM, and IgA (immunoglobulin G, M and A, respectively, represented by intermediate 250 derived along line 252 and formulated into purified IgG product 280 along line 20. Similarly, exemplary components of fraction 190 include alpha$_1$ proteinase inhibitor and anti-thrombin III, generally represented by intermediate 260 as indicated as being separated along line 262. Note that albumin 270, a product of fraction 200 is pasteurized by incubation at 60° Centigrade for not less than ten hours.

Of primary focus are treating of process intermediates 250 and 260 to inactivate both enveloped and non-enveloped viruses. Each such process intermediate is treated according to the present invention by application of an SD treatment in conjunction with addition of either formaldehyde or phenol or a combination of both formaldehyde and phenol in controlled concentrations, see lines 20 and 20'. (Similarities of processes associated with lines 20 and 20' are emphasized by using a prime of 20 as an indicator of treating intermediate 260.) So treated each process intermediate 250 and 260 yields a purified product 280 and 290, respectively. Product 280 is symbolized by (IgG) and product 290 is symbolized by (Alpha$_1$ Proteinase Inhibitor, $\alpha_1$–PI, Antithrombin-III).

Each SD and formaldehyde/phenol virus inactivation process, generally numbered 30 in FIG. 1, may be performed in alternative sequences of applying SD and a formaldehyde/phenol mixture to process intermediates 250 and 260 (250/260 in FIGS. 2–4). Examples of allowable variations is such sequences are seen in FIGS. 2–4. It should be clear to those skilled in the art of blood plasma fractionation that other variations of alternate sequences are possible within the scope of the instant invention.

As seen in FIG. 2, SD and formaldehyde/phenol treatments (SD/FP Treatment 300) are performed concurrently. To accomplish a concurrent SD/FP treatment 300, SD chemicals are added according to standard protocol for each selected SD treatment (various manufacturers or vendors may have individually defined protocols for their particular product). Formaldehyde and/or phenol ingredients are added to the mixture of intermediates 250/260 to produce a final concentration of each ingredient in the range of 100 to 10,000 parts per million (although other concentrations may be used within the scope of the instant invention when appropriately qualified). Incubation period and temperature may also follow protocol for the selected SD treatment (see line 310), which is usually within bounds of a temperature between fifteen and forty-five degrees Centigrade for a period of one to twelve hours. At the end of the incubation period, the process yields an intermediate with SD/FP chemicals, an intermediate 320 comprises a residual of purified intermediates and SD/FP chemicals. The SD and FP chemicals are removed by a process indicated by line 330 which may follow a protocol for removal of SD chemicals for the selected SD treatment to produce a purified product, 280 or 290 (see FIG. 1), identified as 280/290 in FIGS. 2–4.

As seen in FIG. 3, a selected SD treatment process 340 is performed separately and before an associated FP treatment process 350. Following SD treatment of intermediates 250/260 (see line 352), SD chemicals are removed (see line 354) from partially purified intermediates 356 (with SD chemicals) to produce a partially SD treated intermediate 358. A protocol similar to the SD treatment protocol (see line 359) may be followed for FP treatment 350, resulting in a residual SD treated intermediate with F/P chemicals 360. Incubation periods and temperatures may follow similar guidelines to those expressed for the process of FIG. 2. FP chemicals are then removed (see line 362), again following chemical removal protocol established for the selected SD treatment to yield a purified product 280/290. It should be noted that other times and temperatures which have been proved safe and effective for FP treatment may also be used within the scope of the instant invention.

As seen in FIG. 4, an FP treatment process 350 is performed separately and before a selected SD treatment process 350. Following FP treatment of intermediates 250/260 (see line 370), FP chemicals are removed (see line 372) from a partially purified (with F/P chemicals) intermediate 374 to produce a first partially processed F/P treated intermediate 376. Removal of FP chemicals (see line 378) may follow chemical removal protocol established for the selected SD treatment, although other removal protocol may be used within the scope of the invention. An SD treatment 340 is performed (see line 380) resulting in an F/P treated intermediate further treated with SD chemicals intermediate 390. SD chemicals are removed (see line 392) to permit recovery of protein and purified product 280/290 following established SD treatment protocol. All incubation periods and temperatures may follow similar guidelines to thos xpressed for the process of FIG. 2.

A number of studies have been performed to ascertain characteristics and effectiveness of a range of F/P concentrations and incubation periods performed according to the instant invention. However, the scope of opportunity for using F/P chemicals, as generally disclosed herein, is too broad to permit performing experiments which cover all possible combinations of concentrations and temperatures and periods of incubation possible within the scope of the present invention.

Generally, inactivating viruses with F/ chemicals may be broadly considered to be a rate reaction. For this reason, a broader range of solution concentrations than those enumerated hereafter may be used with varying incubation temperatures and periods. However, great care should be taken to prequalify each new protocol defining new concentrations and incubation temperature and period to assure safety and effectiveness of each new candidate process associated with the instant invention. As an example, stronger solutions may be applied for shorter time periods (at predetermined temperatures and times of reaction) or a more dilute solution may be incubated for a longer time to achieve substantially the same virus inactivation. Similarly, if a manufacturer specifies a higher temperature, then a weaker concentration of the F/P sterilant may be used to achieve results within the time period indicated by the manufacturer.

Within the scope of experiments performed to date, the range of F/P concentrations are generally from 100 ppm (0.01%) to 10,000 ppm (1%). More specifically, concentrations from 1000 ppm to 5,000 ppm at a suggested temperature of 27° C. for a minimum six hour incubation period may be considered. It is currently preferred in these cases that equal concentrations of formaldehyde and phenol be employed.

During experimentation, it was noticed that a portion of formaldehyde is "used up" during a virus inactivating process. As an example, in one experiment using 250 ppm formaldehyde for a twenty to thirty minute incubation, 50 to 80 ppm had been lost to the cells in some manner. At the end of the incubation period only 170 to 200 ppm was left to be separated via the wash.

Following is a summary of studies performed:

Stability Study

Objective

To ascertain if any degradation (no denaturation nor complexing nor crosslinking) of a gamma globulin solution occurs when different amounts of sterilant are added to a base solution of human gamma globulin.

Procedure

Human Gamma Globulin powder was stored at −20° C. (Lot #0D021 from Beckman Instruments). A 4% solution was made in normal saline. The solution was stirred for 2 hours at room temperature. The solution was allowed to sit overnight at +5C. This solution was spun down at 3500 RPM for 10 minutes to remove any material not in solution. The spun solution was collected and filtered thru Whatman #1 to remove any "fines" in solution. The end material was stored in an amber glass container at +5° C. thru these experiments.

Result

The solution collected was clean and slightly opalescent.

Experiment #1

Objective

Determine whether or not processing by chemical solutions made according to the instant invention cause denaturation of protein or cross-linking (aggregation) of the proteins.

Procedure

A stock of the following solutions was prepared in the concentrations indicated:

Solution #1

Formaldehyde (HCHO) at 50,000 ppm was prepared by diluting Formaldehyde solution [37% (370,000 ppm)] to 50,000 ppm by adding 13.5 ml of HCHO to 86.5 ml of saline with stirring. Final Formaldehyde dilution in the solution was 50,000 ppm (5% HCHO).

Solution #2

Phenol—50,000 ppm.

Five grams of crystalline phenol was added to 95 ml of saline. After solution stirring, the resultant solution was diluted to 100 ml with saline, resulting in a final concentration of phenol of 50,000 ppm.

Solution #3

Formaldehyde/Phenol solution 50,000 ppm each. One gram of phenol was added to 20 ml of solution #1 above—after stirring, concentration of each sterilant was 50,000 ppm.

Procedure

A study involving application of reagents as prepared above to a gamma globulin solution was run against a blank (untreated gamma globulin solution). Measurements of optical density were made using a Beckman DU-7 Spectrophotometer with Peltier cooling (to hold a temperature setpoint within 0.1° degree C from what is set up). Beckman 1 cm quartz cuvettes were used to measure the optical density at 630 nm against a water blank. Values were measured for 2 hours at 27° C. against the water blank. The untreated gamma globulin solution with no additions was measured as well as gamma globulin to which prepared solutions had been added such that final concentration was 3,000 ppm formaldehyde (HCHO), 3,000 ppm phenol, and a combination of HCHO/Phenol at 3,000 ppm each.

Results

Any denaturation of the protein should result in an early increase in the optical density. Any cross-linking (aggregation) of the proteins, is expected to result in a decrease in optical density as the protein will precipitate (fall-out) of solution.

Initial reading at time 0 was used to determine a rough baseline. The solution took about 5 minutes to reach temperature with 3 ml per cuvette.

Results ar summarized in Table III, below:

TABLE III

Optical Density of the Solutions

| Time min. | Blank Water | Gamma G Control | HCHO | Phenol | HCHO/Phenol |
|---|---|---|---|---|---|
| 0 | 0.000 | 0.063 | 0.058 | 0.071 | 0.059 |
| 30 | 0.000 | 0.062 | 0.059 | 0.070 | 0.061 |
| 60 | 0.000 | 0.062 | 0.060 | 0.069 | 0.062 |
| 90 | 0.000 | 0.061 | 0.060 | 0.068 | 0.062 |
| 120 | 0.000 | 0.061 | 0.062 | 0.068 | 0.063 |

RESULTS

Within the error of the measurements, there was no observed change in the optical density of the different solutions and therefore there is neither crosslinking nor denaturation of the gamma globulin proteins when made up as a solution treated with the different sterilant solutions.

Experiment 2

Objective

Determine antibody responses of gamma globulin solutions and sterile treated gamma globulin solutions to various levels of formaldehyde, i.e. 250 ppm, 500 ppm, 1000 ppm, and 3000 ppm.

The purpose of this experiment was to demonstrate that when formaldehyde is added to a protein solution of gamma globulin, that it will not cross-link nor denature the protein so that it will not function.

Procedure

Gamma globulin solutions employed contained antibodies for the blood types of A and B because the solutions were gathered from many donors and pooled. Th level of antibodies were not at a high titer but they were known to be in the sample blood which was typed as AB in this experiment. Cells were removed from the blood bag and washed 3 times in saline to remove all proteins from the red blood cells (RBC). The RBC were then adjusted to a 5% concentration level of cells in saline and stored at +5° C. during the experiment. Three drops of cells were put into the bottom of a 12×75 mm glass test tube. Three drops of protein solution were put into the test tube and mixed with the cells. The mixture was allowed to react for 3 minutes and then spun down for five minutes in a blood bank mini-centrifuge designed for blood bank operations. The tubes were carefully removed from the centrifuge bowl and the blood mass at the tip of the tube was very gently rocked back and forth to determine if an antigen-antibody reaction had taken place to form a stable button. Test solutions were prepared from the gamma globulin solution made in Experiment #1 above. They were used as a control solution (nothing added to the gamma globulin solution), and gamma globulin solutions treated with formaldehyde treated gamma globulin solutions at 250, 500, 1000, and 3000 ppm. Treatment was begun and reactions were measured at zero (0) time, at 4 hours, 6 hours and 24 hours to determine if there was any interference with the AB agglutinating ability of the gamma globulin solutions. It should be noted that, if the addition of the formaldehyde caused any crosslinking or degradation of the gamma globulin solutions, the test solutions would not agglutinate properly. Note also that zero time (0) is actually about 5 minutes after addition of the sterilants. The measurements are summarized in Table IV below:

TABLE IV

Agglutination Study

| TIME | | ppm formaldehyde added | | | |
|---|---|---|---|---|---|
| Hours | Control | 250 | 500 | 1000 | 3000 |
| 0 | button | button | button | button | button |
| 4 | button | button | button | button | button |
| 6 | button | button | button | button | button |
| 24 | button | button | button | button | button |

RESULTS

This experiment showed that there was no interference due to any type of crosslinking or degradation (denaturation) of the gamma globulin after the addition of the formaldehyde solutions. All of the agglutination reactions noted are identical to the control solution (untreated).

Experiment #3

Objective

Observe effects of application of solutions made according to the invention and applied to samples to determine changes, if any, in amino acids that make up gamma globulin solutions.

Procedure

This experiment involved electrophoresis of the gamma globulin solutions. A Beckman serum protein electrophoresis kit was obtained and used to electrophorese the gamma globulin solutions described in Experiment #1 above. A control solution (no treatment), and gamma globulin solutions treated with formaldehyde at 3000 ppm, phenol at 3000 ppm and the combination of formaldehyde/phenol at 3000 ppm each were prepared.

The reason for subjecting protein to an electrophoresis test is, should there be changes in the amino acids that make up the gamma globulin solutions, then such changes cause the proteins to migrate at a different rates thereby demonstrating subsequent changes in electrophoresis patterns. In the case of hemoglobin electrophoresis, the globin portion of hemoglobin consists of some 574 amino acids and if even one is changed, the pattern modified protein moves to a different position of the gel, providing a definite visual difference. Such a difference is easily seen, for example, between Hemoglobins A and F and S.

Electrophoresis, with 0.5 μl of protein on a narrow strip of an agar gel, was run at 100 volts DC for 25 minutes in a barbital buffer for each test sample. Afterwards the gels were stained and scanned at 600 nm in a densitometer, which is standard treatment.

Results

In all cases (both controls and experiments), the patterns were substantially the same. There was a single band of protein. There were no subdivisions or splitting of the patterns. Nothing propagated differently than the controls. Noting that, if even one of the amino acids making up the gamma globulin molecule were altered, then the charge on the whole molecule would change and propagation would be quite different and observable on the stained patterns.

Conclusions

In these three (3) experiments treating human gamma globulin with formaldehyde, or phenol, or a combination of formaldehyde and phenol, no change occurring to the gamma globulin itself has been measured or seen. There is no crosslinking or denaturation, no change in optical density. Ability to agglutinate is the same with and without being treated by solutions of formaldehyde and phenol made and used according to the instant invention. Similarly, electrophoretic patterns were not substantively altered.

Therefore, addition of either or both of the two sterilants to agument the inactivation of viruses along with the standard SD treatment or even independently of the SD treatment in the fractionation of plasma does not cause meaningful changes in the gamma globulin. However, when used as disclosed herein with an SD solution treatment, the resulting combination is effective against both enveloped and non-enveloped viruses present in blood plasma process intermediates.

Following are six examples of various augmented solutions used for virus inactivation within the scope of the instant invention:

Example 1

An IgG intermediate fraction is brought to 0.5% Triton X-100, 0.5% Tween 80 and, 0.3% TNBP at 27° C. The solution is mixed and then brought to 3000 ppm (0.3%) of formaldehyde and 3000 ppm (0.3%) of phenol by addition from a concentrate of the two sterilants. The solution is then incubated at 27° C. (±3° C.) for 6 to 6.5 hours. The incubated solution is appli d to a previously equilibrated column of CM Sephadex C-50 under conditions that bind the IgG. The sterilants do not bind. The column is washed with buffer to reduce any sterilant levels and then the IgG is removed by elution with a high salt buffer. In this example both sterilants are being used simultaneously to inactivate viruses and are then concurrently removed from the treated IgG.

Example 2

An IgG intermediate fraction is brought to 0.5% Triton X-100, 0.5% Tween 80 and, 0.3% TNBP at 27° C. The solution is then incubated at 27° C. (±3° C.) for 6 to 6.5 hours. Then the solution is brought to 3000 ppm (0.3%) of formaldehyde and 3000 ppm (0.3%) of phenol by addition from a concentrate of the two sterilants. The new solution is then re-incubated at 27° C. (±3° C.) for another 6 to 6.5 hours. The incubated solution is applied to a previously equilibrated column of CM Sephadex C-50 under conditions that bind the IgG. The sterilants do not bind. The column is washed with buffer to reduce any sterilant levels and then the IgG is removed by elution with a high salt buffer. This example demonstrates treating an intermediate product with one sterilant for a defined time period and at a specified temperature and then treating the intermediate treated product with a second sterilant for a defined time period at a specified temperature. This example demonstrates sequential sterilization of intermediate products. The first sterilant addition will have a longer treatment time than the second sterilant by the time the entire sterilization process is compl ted.

Example 3

An IgG intermediate fraction is brought to 0.3% formaldehyde and 0.3% phenol at 27° C. The solution is then incubated at 27° C. (±3° C.) for 6 to 6.5 hours. Then the solution is mixed and then brought to 0.5% Triton X-100, 0.5% Tween 80 and, 0.3% TNBP. The new solution is then incubated at 27° C. (±3° C.) for 6 to 6.5 hours. The incubated solution is applied to a previously equilibrated column of CM Sephadex C-50 under conditions that bind the IgG. The sterilants do not bind. The column is washed with buffer to reduce any sterilant levels and then the IgG is removed by elution with a high salt buffer. This example demonstrates treating an intermediate product with one sterilant for a defined time period and at a specified temperature and then treating the same product with a second sterilant for another defined time period at a specified temperature. This sequential example reverses the order of the addition of the two sterilants as indicated in example 2. The first sterilant addition will have a longer treatment time than the second sterilant by the time the entire sterilization process is completed.

Example 4

An IgG intermediate fraction is brought to 0.5% Triton X-100, 0.5% Tween 80 and, 0.3% TNBP at 27° C. The solution is then incubated at 27° C. (±3° C.) for 6 to 6.5 hours. The incubated solution is applied to a previously equilibrated column of CM-Sephadex C50 under conditions that bind the IgG. The sterilants do not bind. The column is washed with buffer to reduce any sterilant levels and then the IgG is removed by elution with a high salt buffer. This IgG intermediate fraction from this first sterilization step is then mixed and then brought to 3000 ppm (0.3%) of formaldehyde and 3000 ppm (0.3%) of phenol by addition from a concentrate of the two sterilants. The new solution is then incubated at 27° C. (±3° C.) for 6 to 6.5 hours. The incubated solution is applied to a previously equilibrated column of CM Sephadex C-50 under conditions that bind the IgG. The sterilants do not bind. The column is washed with buffer to reduce any sterilant levels and then the IgG is removed by elution with a high salt buffer. This example demonstrates treating an intermediate product with one sterilant for a defined time period and at a specified temperature. The sterilant is removed from the intermediate product which is then treated with a second sterilant for a defined time period at a specified temperature. The second sterilant is removed and the intermediate product purified. This is an example of a sequential treatment using two sterilants wherein the time/temperature treatment may be the same or different for each sterilant.

Example 5

An IgG intermediate fraction is brought to 0.3% formaldehyde and 0.3% phenol at 27° C. The solution is then incubated at 27° C. (±3° C.) for 6 to 6.5 hours. The incubated solution is applied to a previously equilibrated column of CM-Sephadex C50 under conditions that bind the IgG. The sterilants do not bind. The column is washed with buffer to reduce any sterilant levels and then the IgG is removed by elution with a high salt buffer. Then the treated solution is mixed and then brought to 0.5% Triton X-100, 0.5% Tween 80 and, 0.3% TNBP. The new solution is then incubated at 27° C. (±3° C.) for 6 to 6.5 hours. The incubated solution is applied to a previously equilibrated column of CM Sephadex C-50 under conditions that bind the IgG. The sterilants do not bind. The column is washed with buffer to reduce any sterilant levels and then the IgG is removed by elution with a high salt buffer. This example exemplifies treating an intermediate product with one sterilant for a defined time period and at a specified temperature. The sterilant is removed from the intermediate treated product which is then treated with a second sterilant for a defined time period at a specified temperature. The second sterilant is removed and the intermediate product purified. This is an example of a sequential treatment using two sterilants wherein the time/temperature treatment may be the same or different for each sterilant, however, in this example the addition order of the sterilants is reversed from example 4.

Example 6

An IgG intermediate fraction is brought to 3000 ppm (0.3%) of formaldehyde and 3000 ppm (0.3%) of phenol by addition from a concentrate of the two sterilants. The solution is then incubated at 27° C. (±3° C.) for 6 to 6.5 hours. The incubated solution is applied to a previously equilibrated column of CM Sephadex C-50 under conditions that bind the IgG. The sterilants do not bind. The column is washed with buffer to reduce any sterilant levels and then the IgG is removed by elution with a high salt buffer. This is an example of a single sterilant solution of formaldhyde and phnol being used to inactivate viruses simultaneously and then removal of the treated IgG. Manufacturrs of plasma products are now used to using this time of incubation and temperature to treat plasma intermediates with the SD treatment. These manufactures are also wary of using these two sterilant chemicals, but it has been shown that they will inactivate both enveloped and non-enveloped viruses from process intermediates without the extra SD treatments. Both of these sterilants are also present in the human body and are bio-degradable in-vivo.

The invention may be embodied in other specified forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for ffecting an augmented SD treatment of biological products, comprising the steps of:
   (a) mixing into the products, SD treatment chemicals following predefined protocol for the use thereof;
   (b) mixing into the products one or more ingredient selected from a group of ingredients consisting of formaldehyde and phenol such that final amounts of each added ingredient is a prequalified concentration;
   (c) incubating a resulting mixture containing the SD treatment chemicals at a first predetermined temperature for a first predetermined period of time
   (d) incubating a resulting mixture containing the ingredients at a second predetermined temperature for a second predetermined period of time;
   (e) separating the treated product from the SD treatment chemicals, and
   (f) separating the treated product from the one or more ingredients.

2. The method according to claim 1 wherein the first predetermined temperature is maintained within a range not less than 15 degrees C and not great r than 45 degrees C 3. The method according to claim 1 wherein the second predetermined temperature is maintained with a range not less than 15 degrees C and not greater than 45 degrees C.

4. The method according to claim 1 wherein the first predetermined temperature and the second predetermined temperature are the same temperature.

5. The method according to claim 1 wherein the first predetermined period of time is not less than one hour and not greater than twelve hours.

6. The method according to claim 1 wherein the second predetermined period of time is not less than one hour and not greater than twelve hours.

7. The method according to claim 1 wherein step(a) is performed separately and at a different time than step (b).

8. The method according to claim 7 wherein step(a) is performed separately and before step (b).

9. The method according to claim 7 wherein step(a) is performed separately and after step (b).

10. The method according to claim 1 wherein step(a) is performed concurrently with step (b).

11. The method according to claim 1 wherein step(e) is performed separately and at a different time than step (f).

12. The method according to claim 11 wherein step(e) is performed separately and before step (f).

13. The method according to claim 11 wherein step(e) is performed separately and after step (f).

14. The method according to claim 1 wherein step(e) is performed concurrently with step (f).

15. The method according to claim 1 wherein the mixing step comprises products mixed to achieve a final concentration which is in the range of 100 to 10,000 ppm.

16. A process for augmenting a solvent detergent blood plasma treatment, said process comprising the steps of selecting a predetermined solvent detergent to be augmented by added ingredients; selecting one or more of the ingredients to be added from a group of ingredients consisting of formaldehyde, phenol and mixtures of formaldehyde and phenol; simultaneously adding the ingredients with the solvent detergent to a plasma process intermediate-to-be-treated such that the final concentration of each added ingredient from the group of ingredients is from about 100 to 10,000 parts per million; incubating said mixture for a predetermined time at a predetermined temperature; and thereafter separating the treated process intermediate from the treatment solvent detergent and other added ingredients.

17. The process according to claim 16 wherein the predetermined time is not less than one hour and not greater than twelve hours.

18. The process according to claim 16 wherein the predetermined temperature is not less than 15 degrees C and not greater than 45 degrees C.

19. A process for augmenting a solvent detergent treatment of a blood plasma process intermediate comprising the steps of selecting a predetermined solvent detergent treatment product for that intermediate; selecting one or more ingredients from a group of ingredients consisting of formaldehyde, phenol and mixtures of formaldehyde and phenol; adding the selected ingredients to the process intermediate such that the final concentration of each added ingredient is from about 100 to 10,000 parts per million; adding, as a next step, an amount of the selected solvent detergent treatment necessary to effect the solvent detergent treatment of the process intermediate; incubating said mixture for a predetermined time and at a predetermined temperature; separating the ingredients and solvent detergent treatment chemicals from the process intermediate to thereby recover the recovery of the desired therapeutic product.

20. The process according to claim 19 wherein the predetermined time is not less than one hour and not greater than twelve hours.

21. The process according to claim 19 wherein the predetermined temperature is not less than 15 degrees C and not greater than 45 degrees C.

22. A process for augmenting a solvent d tergent treatment of a blood plasma process intermediate comprising the steps of selecting a predetermined solvent detergent treatment product for that intermediate; selecting one or more ingredients from a group of ingredients consisting of formaldehyde, phenol and mixtures of formaldehyde and phenol; adding, an amount of the selected solvent detergent treatment necessary to effect the solvent detergent treatment of the process intermediate; adding, as a next step, the selected ingredients to the process intermediate such that the final concentration of each added ingredient is from about 100 to 10,000 part per million; incubating said mixture for a predetermined time and at a predetermined temperature; separating the ingredients and solvent detergent treatment chemicals from the process intermediate to thereby recover the recovery of the desired therapeutic product.

23. The process according to claim 22 wherein the predetermined time is not less than one hour and not greater than twelve hours.

24. The process according to claim 22 wherein the predetermined temperature is not less than 15 degrees C and not greater than 45 degrees C.

25. A process for augmenting solvent detergent treatment of a blood plasma process intermediate comprising the steps of selecting a predetermined solvent detergent treatment product for that intermediate; selecting one or more ingredients from a group of ingredients consisting of formaldehyde, phenol and mixtures of formaldehyde and phenol; adding the selected ingredients to the process intermediate such that the final concentration of each added ingredient is from about 100 to 10,000 parts per million; incubating the resulting mixture for a first predetermined time at a first predetermined temperature; separating out the added ingredients to recover the desired partially processed process intermediate; adding the selected solvent detergent treatment product necessary to effect the solvent detergent treatment of the recovered process intermediate; incubating said mixture for a second predetermined time at a second predetermined temperature; and separating out the treatment chemicals, thereby recovering the desired therapeutic product.

26. The process according to claim 25 wherein the first predetermined time is not less than one hour and not greater than twelve hours.

27. The process according to claim 25 wherein the first predetermined temperature is not less than 15 degrees C and not greater than 45 degrees C.

28. The process according to claim 25 wherein the second predetermined time is not less than one hour and not great r than twelve hours.

29. The process according to claim 25 wherein the second predetermined temperature is not less than 15 degrees C and not greater than 45 degrees C.

30. A process for augmenting a blood plasma process intermediate solvent detergent treatment comprising the steps of selecting a solvent detergent treatment product for the purpose for treating a process intermediate; adding to the process intermediate, the selected solvent detergent treatment product; incubating said mixture for a first predetermined time at a first predetermined temperature; separating out the treatment chemicals, thereby, recovering a partially processed desired therapeutic product; selecting one or more ingredients from a group of ingredients consisting of formaldehyde, phenol and mixtures thereof; adding the ingredients to the partially processed therapeutic product such that the final concentration of each added ingredient is at a concentration from about 100 to 10,000 parts per million; incubating said mixture for a second predetermined time at a second predetermined temperature; and, thereafter, separating the treating ingredients from the processed process intermediate to thereby recover a desired therapeutic product.

31. The process according to claim 30 wherein the first predetermined time is not less than one hour and not greater than twelve hours.

32. The process according to claim 30 wherein the first predetermined temperature is not less than 15 degrees C and not greater than 45 degrees C.

33. The process according to claim 30 wherein the second predetermined time is not less than one hour and not greater than twelve hours.

34. The process according to claim 30 wherein the second predetermined temperature is not less than 15 degrees C and not greater than 45 degrees C.

35. An immunoglobulin preparation for use in humans or animals prepared by a process comprising the steps of mixing into an initial process intermediate, SD treatment chemicals following predefined protocol for the use thereof; further mixing into the preparation one or more ingredient selected from a group of ingredients consisting of formaldehyde and phenol such that final concentration of each added ingredient ranges from about 100 to 10,000 parts per million; incubating the resulting mixture containing the SD treatment chemicals and ingredients at a predetermined temperature for a predetermined period of time; separating the treated product from the SD treatment chemicals and the one or more ingredients to thereby provide the desired immunoglobulin preparation.

36. An immunoglobulin preparation for use in humans or animals prepared by a process comprising inactivated enveloped and non-enveloped viruses resulting from mixing and incubating a raw form of the immunoglobulin preparation with SD treatment chemicals following predefined protocol for the use thereof; further mixing into the raw preparation one or more ingredients selected from a group of ingredients consisting of formaldehyde and phenol such that final concentration of each added ingredient ranges from about 100 to 10,000 parts per million; incubating the resulting mixture containing the SD treatment chemicals and ingredients at a predetermined temperature for a predetermined period of time; separating the treated product from the SD treatment chemicals and the one or more ingredients to thereby provide the desired immunoglobulin preparation.

* * * * *